United States Patent
Otsubo

(10) Patent No.: US 8,114,236 B2
(45) Date of Patent: *Feb. 14, 2012

(54) METHOD FOR MAKING DISPOSABLE PANTS-TYPE DIAPER

(75) Inventor: Toshifumi Otsubo, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 209 days.

This patent is subject to a terminal disclaimer.

(21) Appl. No.: 12/522,588

(22) PCT Filed: Nov. 16, 2007

(86) PCT No.: PCT/JP2007/072303

§ 371 (c)(1),
(2), (4) Date: Jul. 9, 2009

(87) PCT Pub. No.: WO2008/084596

PCT Pub. Date: Jul. 17, 2008

(65) Prior Publication Data

US 2010/0038018 A1  Feb. 18, 2010

(30) Foreign Application Priority Data

Jan. 12, 2007  (JP) ................................. 2007-005151

(51) Int. Cl.
 *B29C 65/00* (2006.01)
 *B32B 37/00* (2006.01)

(52) U.S. Cl. ........ 156/164; 156/160; 156/163; 156/229; 156/250; 156/267; 156/269; 156/270; 156/324; 156/494; 156/495; 156/496

(58) Field of Classification Search .................. 156/160, 156/163–164, 229, 250, 267, 269–270, 324, 156/494–496

See application file for complete search history.

(56) References Cited

U.S. PATENT DOCUMENTS 4,573,990 A  3/1986  Ohsaki
(Continued)

FOREIGN PATENT DOCUMENTS

GB  2287393 A  9/1995
JP  60-114258 A  6/1985
(Continued)

OTHER PUBLICATIONS

International Search Report of Application No. PCT/JP2007/072303 mailed Jan. 15, 2008.

*Primary Examiner* — Khanh P Nguyen
*Assistant Examiner* — Carson Gross
(74) *Attorney, Agent, or Firm* — Lowe, Hauptman, Ham & Berner, LLP

(57) ABSTRACT

Disclosed is a method of continuously making a disposable pants-type diaper having a body waste receiving pocket. A first web is continuously fed in a machine direction and a second web is continuously fed onto the first web and is folded back onto itself in a cross direction and locally bonded together along opposite edges thereof to obtain a third web. The third web is superposed on the first web and then the first web and the third web are bonded to each other to obtain a first composite web. From between the adjacent chassis in a second composite web defined by the first and third webs, substantially semicircular web pieces are clipped out to obtain third composite web on both sides of a cutting line to obtain a fourth composite web which is cut along the cutting line to obtain the individual pants-type diapers.

14 Claims, 9 Drawing Sheets

U.S. PATENT DOCUMENTS

| | | | | |
|---|---|---|---|---|
| 5,711,832 A | * | 1/1998 | Glaug et al. | 156/73.1 |
| 6,391,013 B1 | * | 5/2002 | Suzuki et al. | 604/385.27 |
| 6,432,248 B1 | * | 8/2002 | Popp et al. | 156/256 |
| 6,508,798 B1 | | 1/2003 | Widlund et al. | |

FOREIGN PATENT DOCUMENTS

| | | |
|---|---|---|
| JP | 05-042180 A | 2/1993 |
| JP | 9-510385 A | 10/1997 |
| JP | 2002-011044 A | 1/2002 |

* cited by examiner

METHOD FOR MAKING DISPOSABLE PANTS-TYPE DIAPER

RELATED APPLICATIONS

The present application is based on International Application Number PCT/JP2007/072303, filed Nov. 16, 2007 and claims priority from, Japanese Application Number 2007-005151, filed Jan. 12, 2007, the disclosures of which are hereby incorporated by reference herein in their entirety.

TECHNICAL FIELD

The present invention relates generally to a method for making a disposable pants-type diaper and particularly to a method for making such pants-type diaper adapted to prevent feces from coming in contact with the wearer's skin.

RELATED ART

There have conventionally been proposed various disposable diapers provided with the functions to protect the wearer's skin being soiled with feces which would otherwise come in contact therewith. For example, the pants-type diaper disclosed in PATENT DOCUMENT 1 includes the skin-contact sheet disposed on the inner sheet and is formed in the crotch region of this skin-contact sheet with the opening surrounded by the elastic member attached under tension to the inner sheet. This opening may be aligned with the wearer's anus to ensure that feces discharged by the wearer moves through the opening into the spaced defined below the skin contact sheet so that feces would not come in contact with the skin. In the case of the method for making the disposable pants-type diaper disclosed in PATENT DOCUMENT 2, the disposable pants having the opening formed in the inner sheet of the diaper is continuously made.

PATENT DOCUMENT 1: JP 2002-11044 A
PATENT DOCUMENT 2: JP 1993-42180 A

DISCLOSURE OF THE INVENTION

Problems to be Solved by the Invention

However, the diaper disclosed in PATENT DOCUMENT 1 still has a problem that feces might move into a space defined between the wearer's skin and the skin-contact sheet and seriously soil the wearer' skin unless the opening formed in the skin-contact sheet is exactly aligned with the wearer's anus. In other words, it is essential for this diaper of prior art to being the opening of the skin-contact sheet in alignment with the wearer's anus in the course of putting the diaper on the wearer's body. However, it can not be determined from the exterior whether the opening of the diaper having been put on the wearer's body is exactly in alignment with the anus or not. Furthermore, the skin-contact sheet is formed with a notch through which urine can be directly absorbed by the absorbent core. Regrettably, urine having passed through the notch will be inevitably mixed with feces on the surface of the absorbent core. Liquidity of feces will increase when it is mixed with urine and consequently a possibility that the wearer's skin might be soiled with feces will correspondingly increase.

In view of the problem left behind unsolved by the conventional diaper as has been described above, it is an object of the present invention to provide a novel disposable pants-type diaper improved to facilitate the wearer's anus to be exactly positioned in opposition to the opening of the feces receiving pocket and thereby to protect the wearer's skin from being soiled with feces.

Measure to Solve the Problem

The object set forth above is achieved, according to the present invention, by an improvement in a method for making a disposable pants-type diaper comprising the continuous steps of preparing a chassis having a crotch region having a back-and-forth direction and a transverse direction which is orthogonal to the back-and-forth direction, a front waist region extending forward from the crotch region and a rear waist region extending rearward from the crotch region wherein transversely opposite side edges of the crotch region extend in the back-and-forth direction, folding back the chassis about the crotch region in the back-and-forth direction, bonding respective inner surfaces of the front and rear waist regions put flat together to each other along transversely opposite side edges of the front and rear waist regions to make the chassis in pants-shape and providing the chassis on its inner surface with a sheet piece forming on the inner surface in the crotch region a pocket adapted to receive body waste. These continuous steps for making the disposable pants-type diaper further comprise the steps as will be described below.

The method according to the present invention further comprises steps of:

a) continuously feeding a first web in a machine direction wherein the first web having a dimension in a cross direction orthogonal to the machine direction bisected by a first center line is adapted to provide successively a plurality of the chassis each having the transverse direction in coincidence with the machine direction as the first web is cut at regular pitches in the machine direction, b) continuously feeding a second web in the machine direction wherein the second web comprising a plurality of the sheet members contiguous one to another in the transverse direction, c) folding the second web back onto itself along a first folding guide line defined by a second center line bisecting the cross direction and locally bonding respective halves of the second web thus folded back to each other along respective edges thereof at same pitches as the pitches so as to obtain a third web having these locally seal regions, d) superposing the first web and the third web upon each other so that the first center line falls in with the first folding guide line formed by the third web in the step c) and the seal regions of the third web fall in with middle regions of the respective chassis, e) locally bonding the third web to the first web in regions thereof destined to form transversely opposite side edges of the crotch region in the chassis or in regions located aside toward the middle regions of respective the chassis as viewed in the machine direction so as to obtain a first composite web having the third web spaced from the regions of the first web destined to define the chassis between the regions in which the first web and the third web are bonded to each other, f) folding back the first composite web along a second folding guide line defined by the first center line with the third web inside and locally bonding the first web to the third web in regions falling in with the regions in which said first web and said third web are bonded to each other in the step e) so as to obtain a second composite web having the third web spaced from regions of the first web destined to define the chassis between the regions in which the first web and the third web are bonded to each other, g) clipping out a substantially semicircular web piece having a chord defined by the second folding guide line and an arc being convex in the cross direction from a region of the second composite web defined between each pair of the adjacent chassis so as to form side edges of the crotch region opposed to each other in the machine direction and thereby to obtain third composite web, h) bonding opposite inner surfaces of the first web folded back onto itself in the third composite web to each other along respectively opposite side edges of the front and rear waist regions in each pair of adjacent the chassis so as to obtain a fourth composite web formed with a linear seal region extending the cross direction, and i) cutting the fourth composite web along a cutting line extending in the cross direction at middle of the seal region as viewed in the machine direction to obtain individual the pants-type diapers successively.

According to one preferred embodiment of the invention, order of the step g) and the step h) is reversed, i.e., the opposite inner surfaces of the first web folded back onto itself in the third composite web are bonded so as to form the linear seal region extending the cross direction and then the web piece is clipped out from the second composite web.

According to another preferred embodiment of the invention, the second web comprises inelastic web fed in the machine direction provided along opposite side edges thereof extending in parallel to each other in the machine direction with elastic members extending in the machine direction and attached under tension thereto.

According to still another preferred embodiment of the invention, the second web is elastically stretchable and contractible in the machine direction and fed under tension in the machine direction.

According to yet another preferred embodiment of the invention, the first web and the third web are locally bonded in the middle region of the crotch region in the chassis as viewed in the back-and-forth direction.

EFFECT OF THE INVENTION

The method for making the disposable pants-type diaper according to the present invention is characterized in that the second web comprising the continuous sheet member adapted to form the pockets in the individual pants-type diapers is continuously fed under tension in the machine direction onto and superposed to the first web continuously fed in the machine direction so as to be continuously bonded thereto. Namely, the second web has no need for any portion having no contribution to the desired function of the pocket such as chucked margins used to tenter the pants-type diaper in the transverse direction. Consequentially, the second web can be economically used in the course of making the pants-type diaper. The second web is superposed on the first web after the second web has been folded back onto itself and these folded halves thereof have been bonded to each other in the middle region of the chassis as viewed in the transverse direction thereof. Consequentially, the presence of the first web would not make it difficult to bond the halves of the folded second web to each other.

Preferred embodiments such method for making the disposable pants-type diaper and effect provided by these preferred embodiments will be described below.

Figure 1:
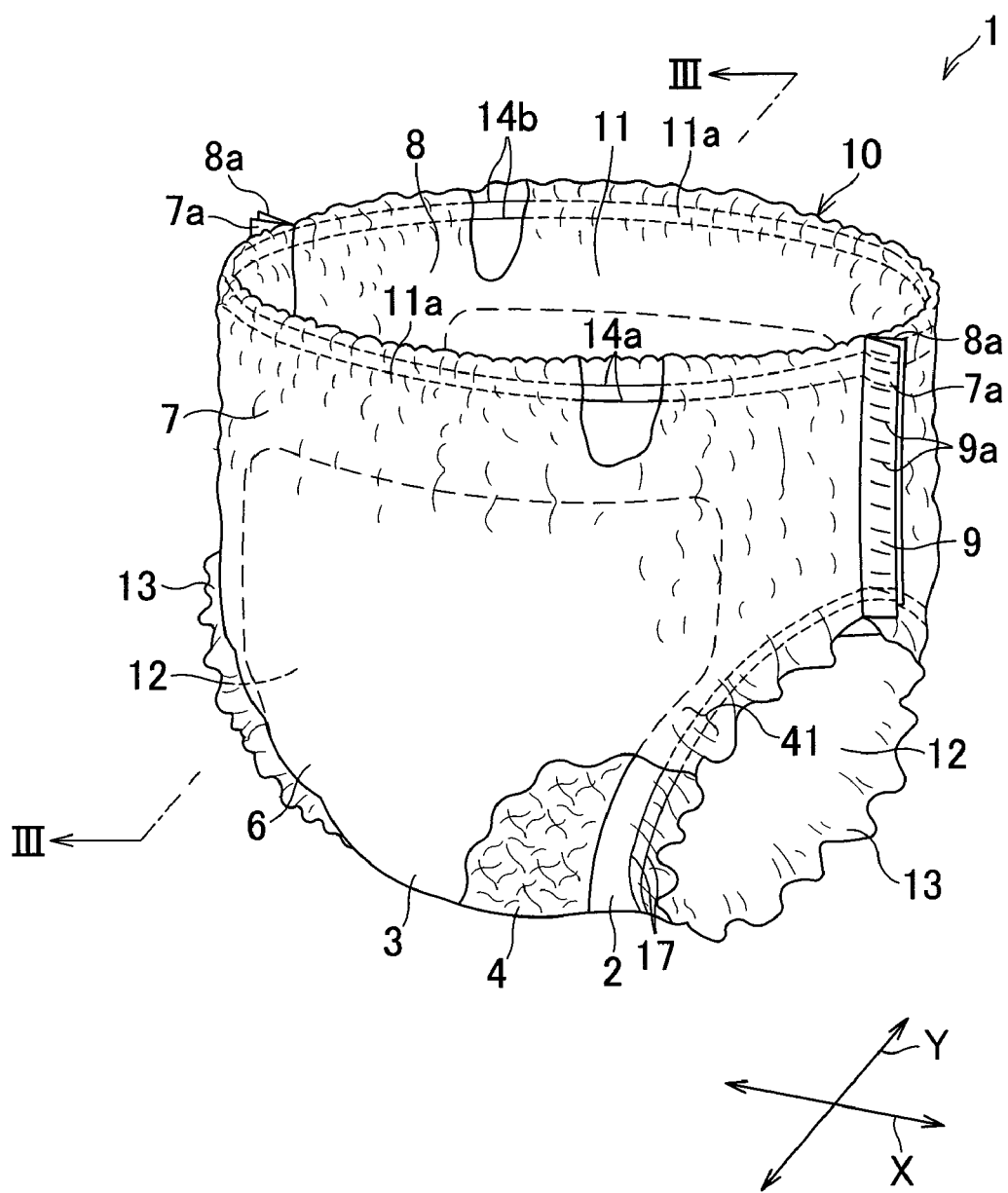
FIG. 1 is a partially cutaway perspective view of a pants-type diaper.

IDENTIFICATION OF REFERENCE NUMERALS USED IN THE DRAWINGS 1 pants-type diaper
6 crotch region
7 front waist region
7a opposite side edge of front waist region
8 rear waist region
8a opposite side edge of rear waist region
9 seal region
10a chassis
12 leg-hole
13 periphery
20 sheet member (sheet piece)
20a pocket
201 first web
202 second web
203 third web
215 web piece
301 first composite web
302 second composite web
303 third composite web
304 fourth composite web
p first center line
q second center line
X transverse direction
Y back-and-forth direction

DESCRIPTION OF THE BEST MODE FOR WORKING OF THE INVENTION

Details of a method for making a disposable pants-type diaper will be more fully understood from the description given hereunder with reference to the accompanying drawings.

FIG. 1 is a partially cutaway perspective view showing a disposable pants-type diaper 1 obtained by a method according to the present invention for making the same as put on the wearer's body. The pants-type diaper 1 has a pants-shaped skin covering assembly 10 comprising a liquid-pervious inner sheet 2, a liquid-impervious outer sheet 3 and a body fluid absorbent core 4 sandwiched between these two sheets 2, 3. The skin covering assembly 10 is configured to define a crotch region 6, a front waist region 7 extending forward from the crotch region 6 and a rear waist region 8 extending rearward from the crotch region 6. The front and rear waist regions 7, 8 are put flat together along respective laterally opposite edges 7a, 8a of thereof and sealed together along these laterally opposite edges in the belt-like seal region 9 in which a plurality of seal stripes 9a are arranged intermittently in a vertical direction as viewed in FIG. 1 so as to form a waist-hole 11 and a pair of leg-holes 12. Sandwiched between the inner and outer sheets 2, 3, a plurality of waist elastic members 14a, 14b circumferentially extend along a periphery defining the waist-hole 11a and are bonded under tension to at least one of the inner and outer sheets 2, 3. In a similar manner, a plurality of leg elastic members 17 sandwiched between the inner and outer sheets 2, 3 circumferentially extend along each periphery 13 defining each of the leg-holes 12 and are bonded under tension to at least one of the inner and outer sheets 2, 3 so that these leg elastic members 17, inner and outer sheets 2, 3 may form loop-shaped elastic regions 41 around the respective legs.

Figure 2:
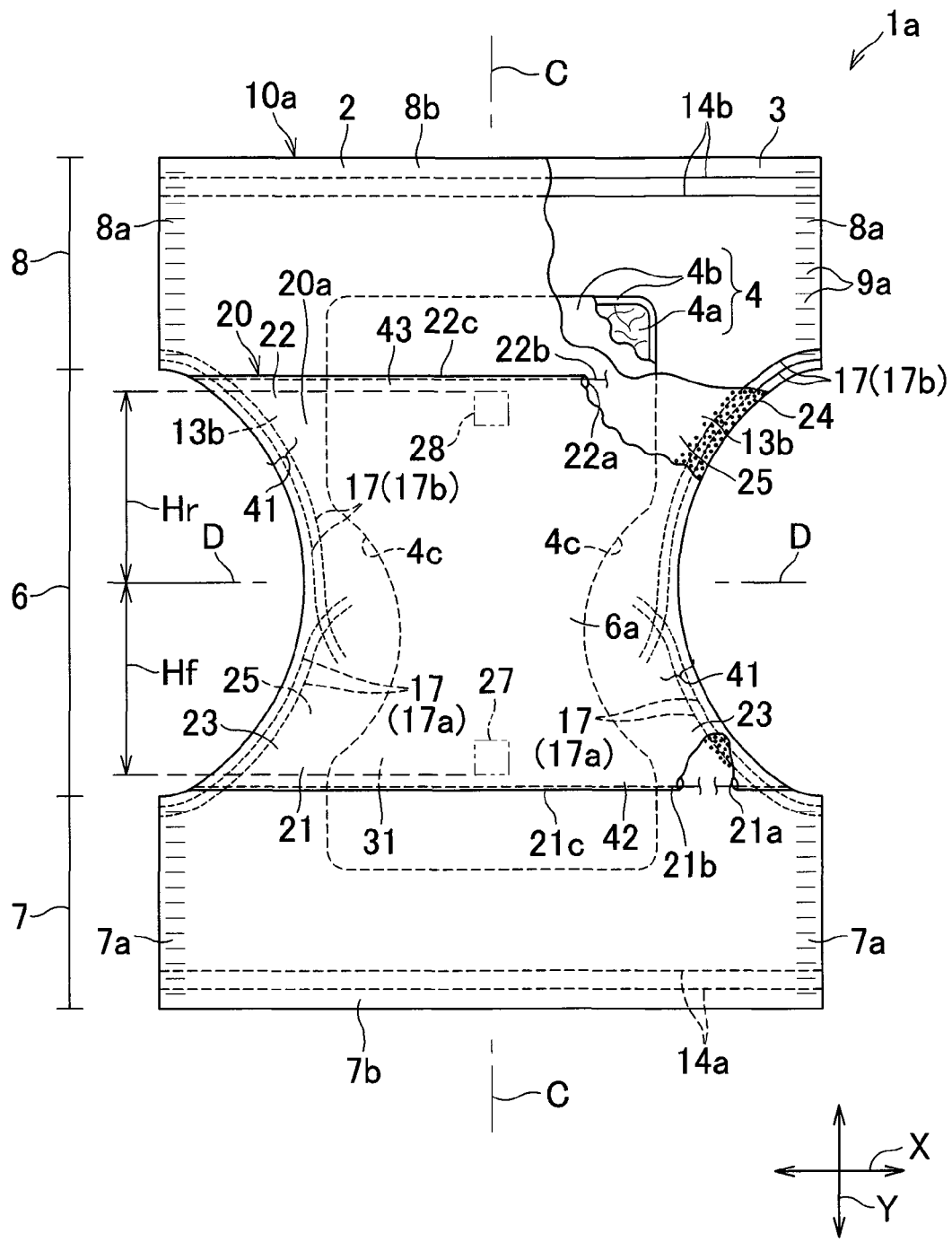
FIG. 2 is a plan view of the pants-type diaper developed in flattened state.

FIG. 2 is a partially cutaway plan view showing a developed diaper 1a corresponding to the pants-type diaper 1 of FIG. 1 having the front and rear waist regions 7, 8 peeled off from each other at the seal stripes 9a and then fully developed in a transverse direction indicated by a double-headed arrow X as well as in a back-and-forth direction indicated by a double-headed arrow Y which is orthogonal to the transverse direction. FIG. 2 shows the inner side of such developed diaper 1a. In the developed diaper 1a, the pants-shaped skin covering assembly 10 corresponds to a chassis 10a having inwardly curved concave shape. The periphery 11a of the waist-hole 11 in FIG. 1 corresponds, in FIG. 2, to a front end 7b and a rear end 8b of the basic structure 10a while the peripheries 13 of the respective leg-holes 12 correspond here to transversely opposite edges 13b of the crotch region of the chassis 10a. While these lateral edges 13b bow toward a longitudinal center line C-C bisecting a width of the chassis 10a, the transversely opposite edges 7a, 8a of the front and rear waist regions 7, 8, respectively, extend in the back-and-forth direction Y substantially in parallel to the longitudinal center line C-C. Leg elastic members 17 extending along the transversely opposite edges 13b of the crotch region 6 respectively consist of front elastic members 17a extending from the middle of the crotch region 6 as viewed in the back-and-forth direction Y toward the front waist region 7 and rear elastic members 17b extending from the middle of the crotch region 6 toward the rear waist region 8 wherein these front and rear elastic members 17a, 17b intersect one with another in the middle of the crotch region 6. The core 4 also has inwardly curved concave shape and comprises a mixture 4a of fluff pulp fibers and super-absorbent polymer particles wrapped with a covering sheet 4b having high absorbability as well as high spreadability for body fluids such as tissue paper. Of the chassis 10a, the inner sheet 2 defining the inner side thereof is provided in the crotch region 6 with a sheet piece 20 preferably made of a hydrophobic sheet material, more preferably made of a hydrophobic and liquid-impervious sheet material so as to form a pocket 20a (See FIG. 3).

The sheet piece 20 has transversely opposite edges 23 fixed to the transversely opposite edges 13b of the crotch region, respectively, by hot melt adhesive 24, a front end 21 lying in the crotch region 6 in the vicinity of the front waist region 7 so as to extend in the transverse direction X to the respective lateral edges 13b of the crotch region 6 and a rear end 22 lying in the crotch region 6 aside toward the rear waist region 8 so as to extend in the transverse direction X to the respective lateral edges 13b of the crotch region 6. Except for the transversely opposite edges 23, the sheet piece 20 is substantially free from the inner sheet 2 so that a tunnel- or pocket-like bodily waste receiving space 31 can be between the sheet piece 20 and the inner sheet 2. The front end 21 and the rear end 22 respectively have sleeves 21a, 22a formed by folding back the respective ends 21, 22 of the sheet piece 20. These sleeves 21a, 22a respectively contain a front elastic member 21b and a rear elastic member 22b attached thereto under tension to form a front elastic region 42 and a rear elastic region 43, respectively, extending between the transversely opposite edges 13b of the crotch region 6. These elastic regions 42, 43 intersect with elastic regions 41 formed by the leg elastic members 17, the inner sheet 2 and the outer sheet 3 in the chassis 10a. The front end 21 and the rear end 22 are substantially at equal distances Hf, Hr from a transverse center line D-D and respectively include a front seal region 27 and a rear seal region 28 indicated by imaginary lines on the longitudinal center line C-C.

Figure 3:
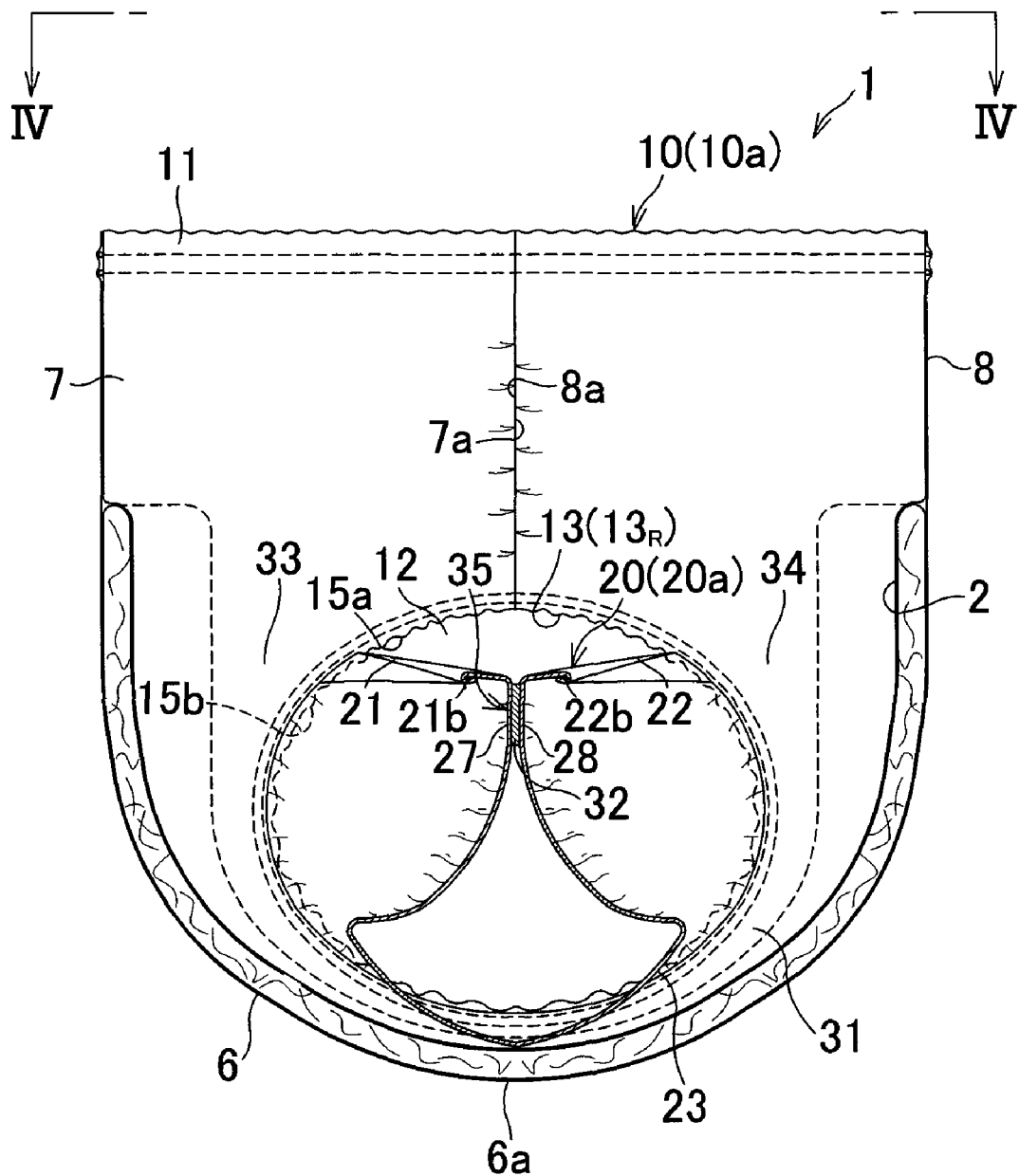
FIG. 3 is a sectional view taken along the line III-III in FIG. 1.

FIG. 3 is a sectional view taken along the line III-III in FIG. 1 wherein the line III-III conforms to the longitudinal center line C-C. The pants-shaped skin covering assembly 10 includes the front waist region 7 and the rear waist region 8 joined together along the transversely opposite edges 7a, 8a, respectively. The crotch region 6 shown in FIG. 2 now bows in FIG. 3 substantially in a U-shape and the transversely opposite edges 13b of the crotch region 6 now appear as the peripheries 13 defining the respective leg-holes 12. The body waste receiving space 31 in the chassis 10a appears here as a pocket 20a defined by a front seal region 27 of the front waist region 21 and a rear seal region 28 of the rear end 22 of the sheet piece 20 permanently bonded together by bonding agent 32 such as hot melt adhesive or pressure-sensitive adhesive so as to form a seal region 35. The pocket 20a has a front opening 33 defined by the front end 21 of the sheet piece 20 corresponding to a front end of the pocket 20a together with the inner sheet 2 and a rear opening 34 defined by the rear end 22 of the sheet piece 20 corresponding to a rear end of the pocket 20a together with the inner sheet 2. At the bottom 6a defined by the lowest portion of the crotch region 6, the inner sheet 2 and the sheet piece 20 are substantially or really in contact with each other.

Figure 4:
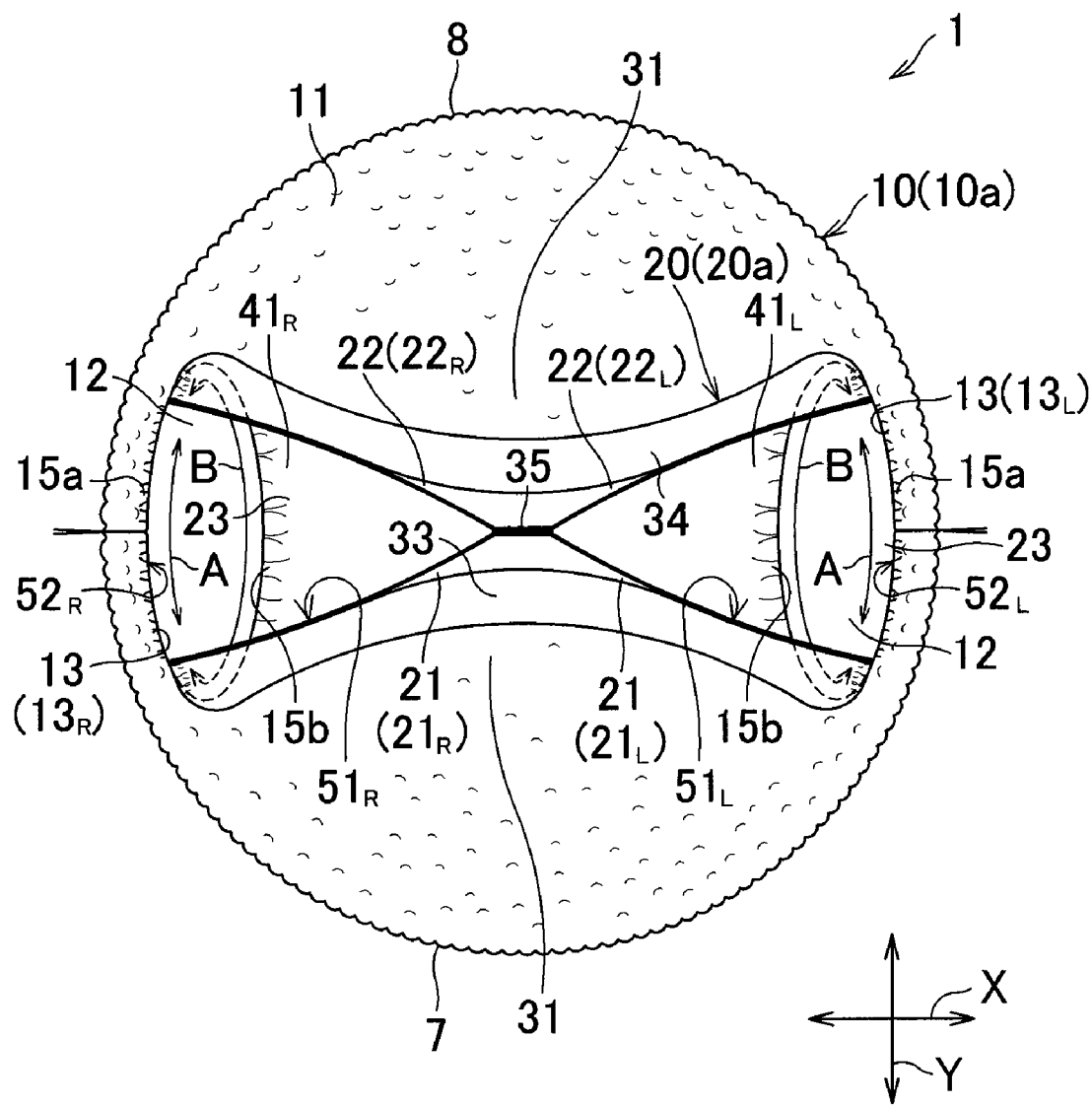
FIG. 4 is a sectional view taken along the line IV-IV in FIG. 3.

FIG. 4 is an overhead view of the diaper 1 as viewed in a direction indicated by the arrow line IV-IV in FIG. 3, i.e., as viewed from above the waist-hole 11. The front end 21 of the sheet piece 20 has its dimension in the transverse direction X bisected by the seal region 35 into a front end segment $21_R$ adapted to be held in close contact with the right leg and a front end segment $21_L$ adapted to be held in close contact with the left leg of the wearer (not shown). These front end segments $21_R$, $21_L$ describe a V-shape in FIG. 4. The rear end 22 also has its dimension in the transverse direction X bisected by the seal region 35. In the same manner as the front end 21, the rear end segment $22_R$ is adapted to be held in close contact with the right leg of the wearer and the rear end segment $22_L$ is adapted to be held in close contact with the left leg of the wearer wherein these rear end segments $21_R$, $21_L$ describe a V-shape in FIG. 4. The respective peripheries 13 of the leg-holes 12 in the skin covering assembly 10 comprise a periphery $13_R$ for the right leg and a periphery $13_L$ for the left leg wherein each of the peripheries $13_R$, $13_L$ is divided into an upper segment 15a not superposed on and left free from the associated lateral edge 23 of the sheet piece 20 and a lower segment 15b joined to the associated lateral edge 23 (See FIG. 3 also). In FIG. 4, a range corresponding to the upper segment 15a and a range corresponding to the lower segment 15b are represented by double-headed arrows A and B, respectively.

A sequence in which the pants-type diaper of such configuration is put on the wearer's body and how the pants-type diaper 1 behaves in the course of being put on the wearer's body will be described. First, the front and rear waist regions 7, 8 of the skin covering assembly 10 are spaced from each other in the back-and-forth direction Y and thereby the waist-hole 11 is broadened as seen in FIGS. 1 and 4. Thereupon, the front end segment $21_R$ for the right leg and the front end segment $21_L$ for the left leg constituting the front end 21 of the sheet piece 20 are deformed about the seal region 35 so as to describe the V-shape and, in a similar way, the rear end segment $22_R$ for the right leg and the rear end segment $22_L$ for the left leg constituting the rear end 22 of the sheet piece 20 are deformed so as to described the V-shape. Such deformation causes the front opening 33 and the rear opening 34 of the pocket 20a to be automatically broadened (See FIG. 3). At the same moment, the front end segment $21_R$ for the right leg and the rear end segment $22_R$ for the right leg are widely spaced from each other while the front end segment $21_L$ for the left leg and the rear end segment $22_L$ for the left leg are widely spaced from each other. Now the right leg of the wearer (not shown) is guided through an opening $41_R$ for the right leg defined by the upper segment 15a of the periphery segment $13_R$ of the associated leg-hole 12, the front end segment $21_R$ for the right leg of the sheet piece 20 and the rear end segment $22_R$ for the right leg of the sheet piece 20. The right leg is guided further through the right leg-hole 12 defined by the upper segment 15a and the lower segment 15b of the periphery segment $13_R$ for the right leg. Then the left leg is guided through an opening $41_L$ for the left leg defined by the upper segment 15a of the periphery segment $13_L$ for the left leg, the front end segment $21_L$ for the left leg and the rear end segment $22_L$ for the left leg. The left leg is guided further through the left leg-hole 12 defined by the upper segment 15a and the lower segment 15b of the periphery segment $13_L$ for the left leg.

In the pants-type diaper 1 put on the wearer's body in the manner as has been described above, the peripheries 13 of the respective leg-holes 12, i.e., the periphery $13_R$ for the right leg and the periphery $13_L$ for the left leg are elastically contractible around the respective holes 12 while the front end 21 and the rear end 22 of the sheet piece 20 are elastically contractible in the transverse direction X. In the vicinity of the right groin, therefore, the upper segment 15a of the periphery $13_R$ for the right leg, the front end segment $21_R$ for the right leg and the rear end segment $22_R$ for the right leg are elastically held in close contact around the right leg to form a primary seal $51_R$ (See FIG. 4) serving to prevent leakage of body fluids from occurring around the right leg. Below the primary seal $51_R$, the lower segment 15b and the upper segment 15a of the periphery $13_R$ cooperate integrally with each other to form a secondary seal $52_R$ (See FIG. 4) serving to prevent leakage of body fluids from occurring around the right leg. This secondary seal $52_R$ functions in a similar manner to the manner in which the leg-surrounding seal in the conventional pants-type diaper function. Just as the case of the right leg, in the vicinity of the left groin, therefore, the upper segment 15a of the periphery $13_L$ for the left leg, the front end segment $21_L$ for the left leg and the rear end segment $22_L$ for the left leg are elastically held in close contact around the left leg to form a primary seal $51_L$. Below the primary seal $51_L$, the lower segment 15b and the upper segment 15a of the periphery $13_L$ cooperate integrally with each other to form a secondary seal $52_L$. The pants-type diaper put on the wearer's body may be sufficiently pulled up along the waist to ensure that the front end 21 and the rear end 22 of the sheet piece 20, in the vicinity of the seal region 35, come in contact with a zone of the wearer's crotch region defined between the wearer's external genital and anus. Even after the pants-type diaper 1 has been put on the wearer's body, the front end 21 as well as the rear end 22 of the sheet piece 20 is maintained spaced from the inner sheet 2 and the front opening 33 as well as the rear opening is maintained widely broadened.

With the pants-type diaper 1 put on the wearer's body in this manner, the sheet piece 20 forming the pocket 20a distinctly divides the wearer's crotch region into a front half and a rear half so that the front opening 33 formed in the front half is reliably opposed to the wearer's external genital and the rear opening 34 is reliably opposed to the anus. Therefore, it is guaranteed that urine discharged from the external genital is guided through the front opening 33 into the pocket 20a while feces discharged from the anus is guided through the rear opening 34 into the pocket 20a. In this way, the pocket 20a or sheet piece 20 effectively prevents urine and/or feces from coming in contact with the wearer's skin. A possibility that urine and feces might be mixed with each other within the bodily waste receiving space 31 is effectively alleviated because the sheet piece 20 is substantially or really maintained in contact with the inner sheet 2 at the bottom 6a of the crotch region 6. Consequentially, an anxiety that a liquidity of feces might be enhanced by admixture of urine and feces is effectively alleviated by the pants-type diaper 1. Even in the unlikely event that urine and/or feces is not guided into the bodily waste receiving space 31 but moves along the wearer's legs, the primary seals $51_R$, $51_L$ and the secondary seals $52_R$, $52_L$ provided around the wearer's legs cooperate together to prevent urine and/or feces from readily moving out beyond the leg-holes 12 of the pants-type diaper 1. Alternatively, the inner sheet 2 and the sheet piece 20 may be bonded to each other locally, for example, merely along the bottom 6a of the crotch region 6 over the full width in order to eliminate the problem that urine and feces might be mixed with each other within the pants-type diaper 1.

In the pants-type diaper 1 provided by the present invention, stock materials for the inner sheet 2 may be selected from the group including a liquid-pervious nonwoven fabric and a perforated plastic film. Stock materials for the outer sheet 3 may be selected from the group including a liquid-impervious plastic film and a laminated sheet consisting of such plastic film and nonwoven fabric. As liquid-absorbent materials for the core 4, a mixture of fluff pulp and super-absorbent polymer particles, or fluff pulp fibers alone, or a mixture of fluff pulp fibers and super-absorbent polymer fibers may be used. For the wrapping sheet 4b, tissue paper often used may be replaced by an appropriate nonwoven fabric. As sheet materials 62 for the sheet piece 20, a hydrophobic, or a hydrophobic and liquid-impervious nonwoven fabric or a plastic film may be preferably used. More preferably, the sheet materials can be elastic or inelastic so long as it is elastically or inelastically extensible in response to elastic extension of the elastic members 21b, 22b. When the sheet piece 20 is elastically contractible, the front elastic member or the rear elastic member can be omitted. If the inner and outer sheets 2, 3 and the other sheet material such as the sheet piece 20 contain any heat-fusible plastics, these sheet materials may be heat-sealed by the known sonic sealing technique.

The sheet piece 20 of the chassis 10a shown by FIG. 2 is attached to the chassis 10a so that the distance Hf from the transverse center line D-D to the front joint region 27 is equal to the distance Hr from the transverse center line D-D to the rear joint region 28. In the case of the sheet piece 20 used in the pants-type diaper 1 for baby, each distance Hf, Hr is preferably in a range of 20 to 150 mm, more preferably in a range of 40 to 80 mm. In addition, a dimension of the front and rear joint regions 27, 28 in the transverse direction X is preferably in a range of 3 to 50 mm, more preferably in a range of 10 to 30 mm. A dimension of the sheet piece 20 in the back-and-forth direction Y is at least 3 mm. Alternatively, it is possible to dimension the sheet piece 20 in the transverse direction X to be less than that in the illustrated embodiment so that the transversely opposite edges 23 thereof may be placed aside from the transversely opposite edges 13 of the chassis 10a toward the center line C-C in the back-and-forth direction.

The chassis 10a of FIG. 2 further includes a pair of side flaps 25 defined by portions of the inner and outer sheets 2, 3 extending outward in the transverse direction X beyond the transversely opposite edges of the core 4. The side flaps 25 have flexural stiffness in the transverse direction X lower than that of the core 4 and are correspondingly easier to be deformed. These side flaps 25 include the leg elastic regions 41. When the pants-type diaper 1 obtained from the chassis 10a is in a state of FIG. 1 wherein the crotch region 6 bows in a U-shape in the front-and-rear direction Y, the side flaps 25 tend to raise themselves up along the lateral opposite edges 4c of the core 4 under contraction of the elastic regions 41 in the vicinity of the transverse center line D-D, i.e., at the bottom 6a of the crotch region 6. On the other hand, the sheet piece 20 is bonded along the transversely opposite edges 23 thereof to the inner surface of the elastic regions 41 by adhesive 24. In response to deformation of the front and rear ends 21, 22 of the sheet piece 20 in a V-shape as shown in FIG. 4 from the state thereof shown in FIG. 2 wherein these front and rear ends 21, 22 rectilinearly extend, these front and rear ends 21, 22 function to pull the side flaps 25 toward the longitudinal center line C-C and thereby enhance the behavior of the side flaps 25 to raise themselves up. The side flaps 25 behaving in this manner are reliably held in close contact around the legs of the wearer from below and thereby effectively prevent leak of body fluids from possibly occurring around the legs. However, if such leakage preventing effect is not required for the pants-type diaper 1, the leg elastic members 17a, 17b may be saved.

FIG. 5 through FIG. 9 are diagrams exemplarily illustrating step of the process for continuously making the pants-type diaper 1 of FIG. 1. In these diagrams, a machine direction is indicated by an arrow MD and a cross direction orthogonal to the machine direction MD is indicated by a double-headed arrow CD.

Figure 5:
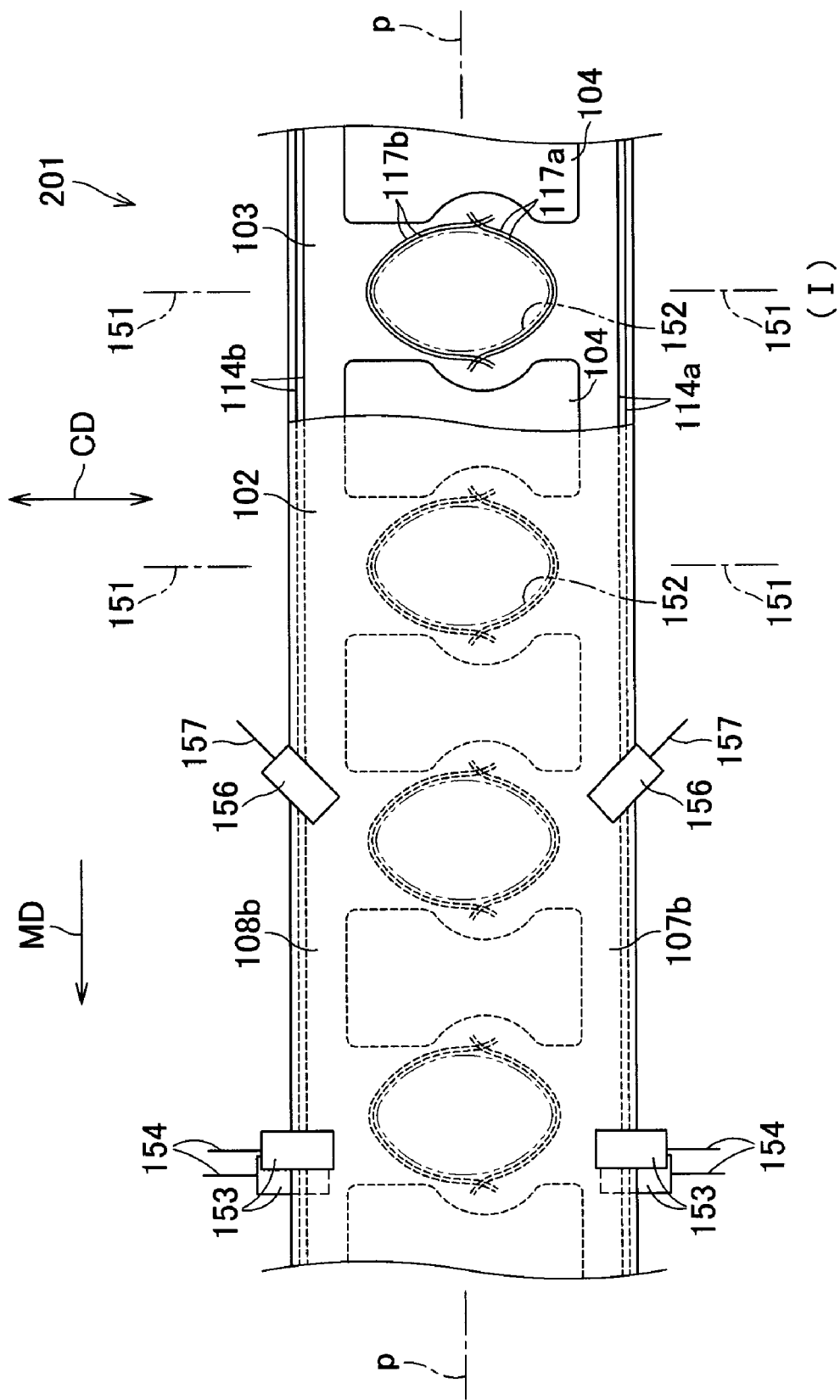
FIG. 5 is a diagram partially illustrating a process for making the pants-type diaper.

In a first step I illustrated in FIG. 5, a first web 201 is continuously fed in the machine direction MD, preferably under tension in the machine direction MD as well as in the CD direction. This first web 201 is laminate consisting of a continuous inner sheet 102 corresponding to the liquid-pervious inner sheet 2 of the chassis 10a (See FIG. 2) which is continuous in its transverse direction X and a continuous outer sheet 103 corresponding to the liquid-impervious outer sheet 3 which has the same width as that of the continuous inner sheet 102 and continuous in its transverse direction X. Between these two continuous inner and outer sheets 102, 103, a plurality of body fluid absorbent cores 104 are sandwiched at regular center intervals each corresponding to the width of the chassis 10a in the machine direction MD and bonded to at least one of these continuous inner and outer sheets 102, 103 by hot meld adhesive (not shown). The continuous inner and outer sheets 102, 103 also are bonded to each other by hot melt adhesive (not shown). An imaginary line 151 extending in the cross direction CD in the middle between each pair of the adjacent cores 104 indicates a position at which the assembly including the first web 201 will be cut in a subsequent step (See FIG. 9) and a dimension between each pair of the adjacent imaginary lines 151, 151 is equal to the width of the chassis 10a. A loop-shaped imaginary line 152 illustrated in the middle region of first web 201 as viewed in the cross direction CD is illustrated to be bilaterally symmetric about the imaginary line 151 and symmetric also in the vertical direction, i.e., in the cross direction CD. This loop-shaped imaginary line 152 indicates a boundary surrounding a region which will be cut away in a subsequent step (See FIG. 9). Immediately outside the imaginary line 152, leg elastic members 117a, 117b extend along the imaginary line 152 so as to be sandwiched between the continuous inner and outer sheets 102, 103 and bonded to at least one of these continuous inner and outer sheets 102, 103 by hot melt adhesive (not shown). These elastic members 117a, 117b respectively trace substantially semicircular courses and intersect one another so as to describe together a loop wherein these elastic members 117a, 117b are under tension at least partially along this loop. The first web 201 is further provided along edges 107b, 108b thereof extending in parallel to each other in the machine direction MD with elastic members 114a, 114b respectively extending under tension in the machine direction MD. These elastic members 114a, 114b are bonded to the inner surface of at least one of the continuous inner and outer sheets 102, 103 by hot melt adhesive (not shown). The opposite edges 107b, 108b of the first web 201 are nipped in thickness direction thereof by associated sets of feed rolls 153, respectively, which are paired in the cross direction and adapted to feed the first web 201 under tension in the machine direction MD. The sets of feed rolls 153 paired in this manner are intermittently disposed at appropriate intervals in the machine direction MD. While axes 154 of these feed rolls 153 are illustrated to extend orthogonally to the machine direction MD, an angle of these axes 154 with respect to the machine direction MD may be appropriately varied, if desired. In addition to these feed rolls 153, tentering rolls 156 paired in the cross direction are disposed in appropriate regions along the opposite edges 107b, 108b so that these tentering rolls 156 may be held in contact with the continuous inner sheet 102 and thereby tenter the first web 201 in the cross direction CD. While axes 157 of the respective tentering rolls 156 are illustrated to intersect with the machine direction MD obliquely at a particular angle, this angle is not limited to the particular angle as illustrated. An imaginary line p-p in FIG. 5 indicates a first center line bisecting the first web 201 in the cross direction CD. It will be appreciated that the first web 201 may be fed in the machine direction MD by any means replacing the rolls 153, 156 used in the illustrated embodiment. In the illustrated embodiment, the first web 201 may be successively cut at a pitch corresponding to a distance between each pair of the adjacent imaginary lines 151, 151 to obtain the chassis 10a in a continuous fashion.

Figure 6:
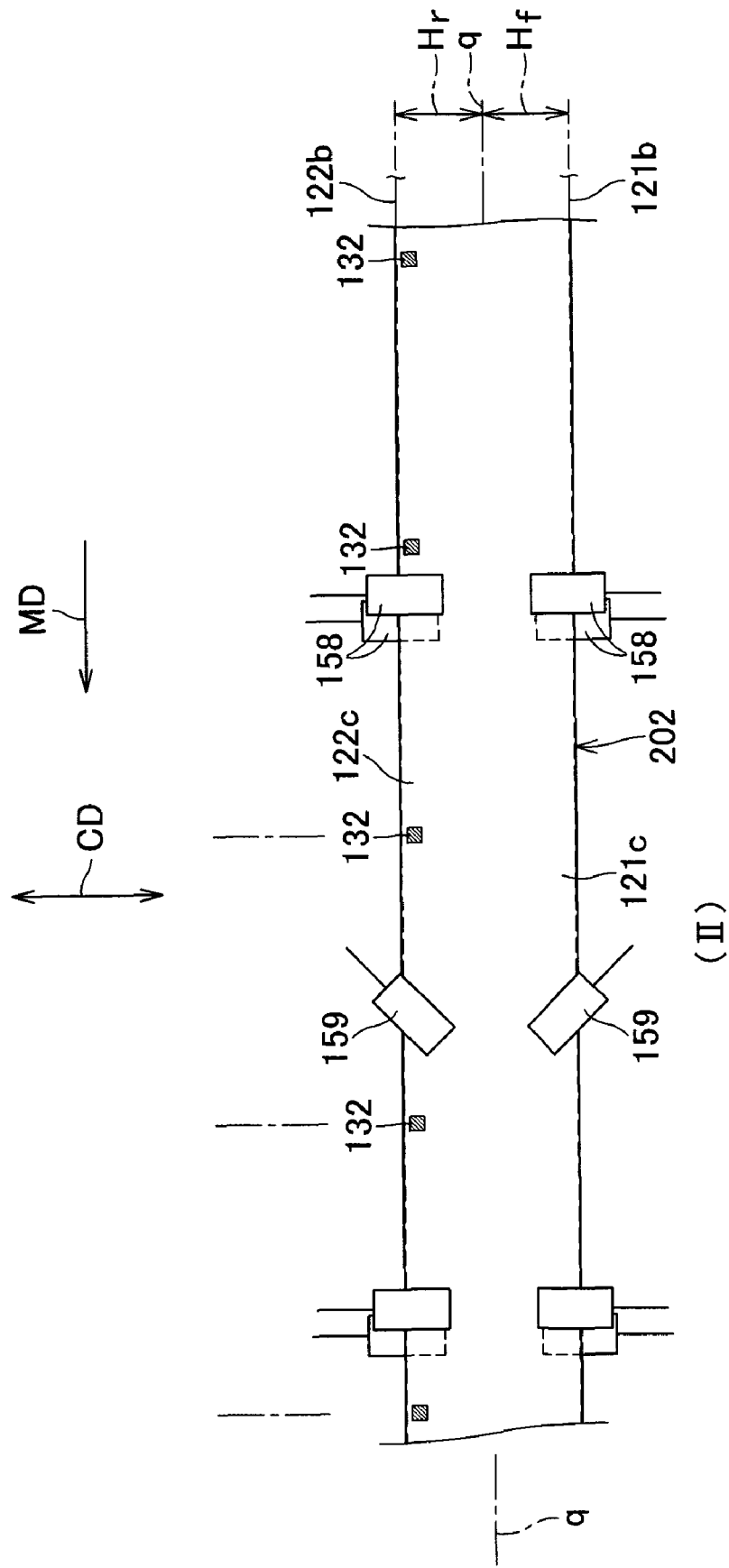
FIG. 6 is a diagram illustrating a step following up a step illustrated in FIG. 5.

In a second step II illustrated in FIG. 6, a second web 202 comprising the sheet pieces 20 destined to be attached to the associated chassis 10a and continuously arranged in the transverse direction X is continuously fed in the machine direction MD preferably under tension in the machine direction MD as well as in the cross direction CD. For this step of feeding, feed rolls 158 and tentering rolls 159 are used. The second web 202 has a pair of edges 121c, 122c extending in parallel to each other in the machine direction MD and the one edge 122c of these edges 121c, 122c is coated at regular pitches each corresponding to the width of the chassis 10a, i.e., corresponding to the distance between each pair of the adjacent imaginary lines 151, 151 as illustrated in FIG. 5 with bonding agent 132 such as pressure-sensitive adhesive. An imaginary line q-q indicated in FIG. 6 defines a second center line bisecting the second web into two dimensions Hf, Hr in the cross direction CD.

Figure 7:
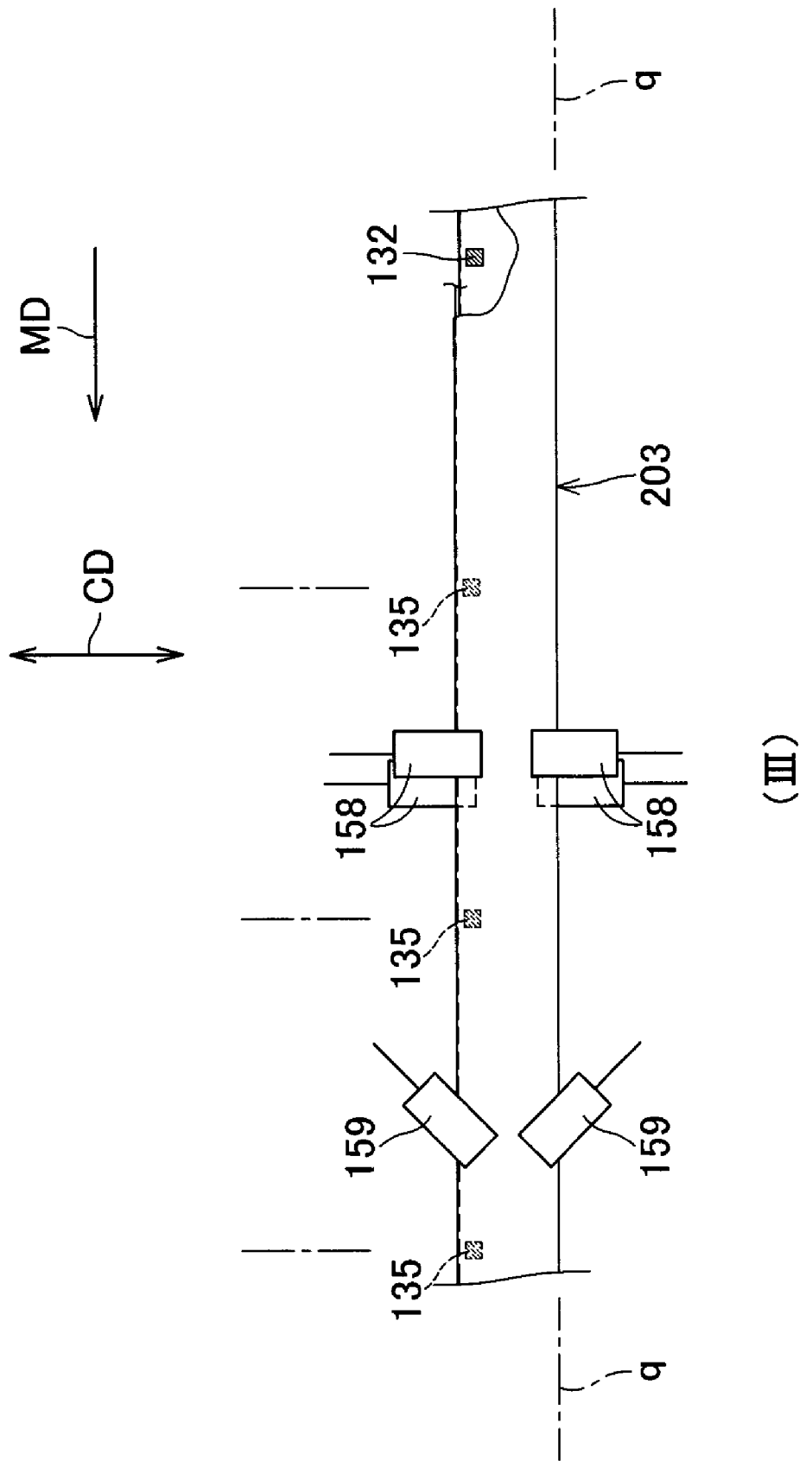
FIG. 7 is a diagram illustrating the step following up the step illustrated in FIG. 6.

In a third step III illustrated by FIG. 7, the second web 202 is folded back onto itself along a folding guide line defined by the second center line q-q with the bonding agent 132 inside and thereby the respective halves of the second web 202 folded back in this manner are locally bonded to each other by the bonding agent 132 to obtain a third web 203 having a seal region 135. The third web 203 also can be fed in the machine direction MD using the feed rolls 158 and the tentering rolls 159.

Figure 8:
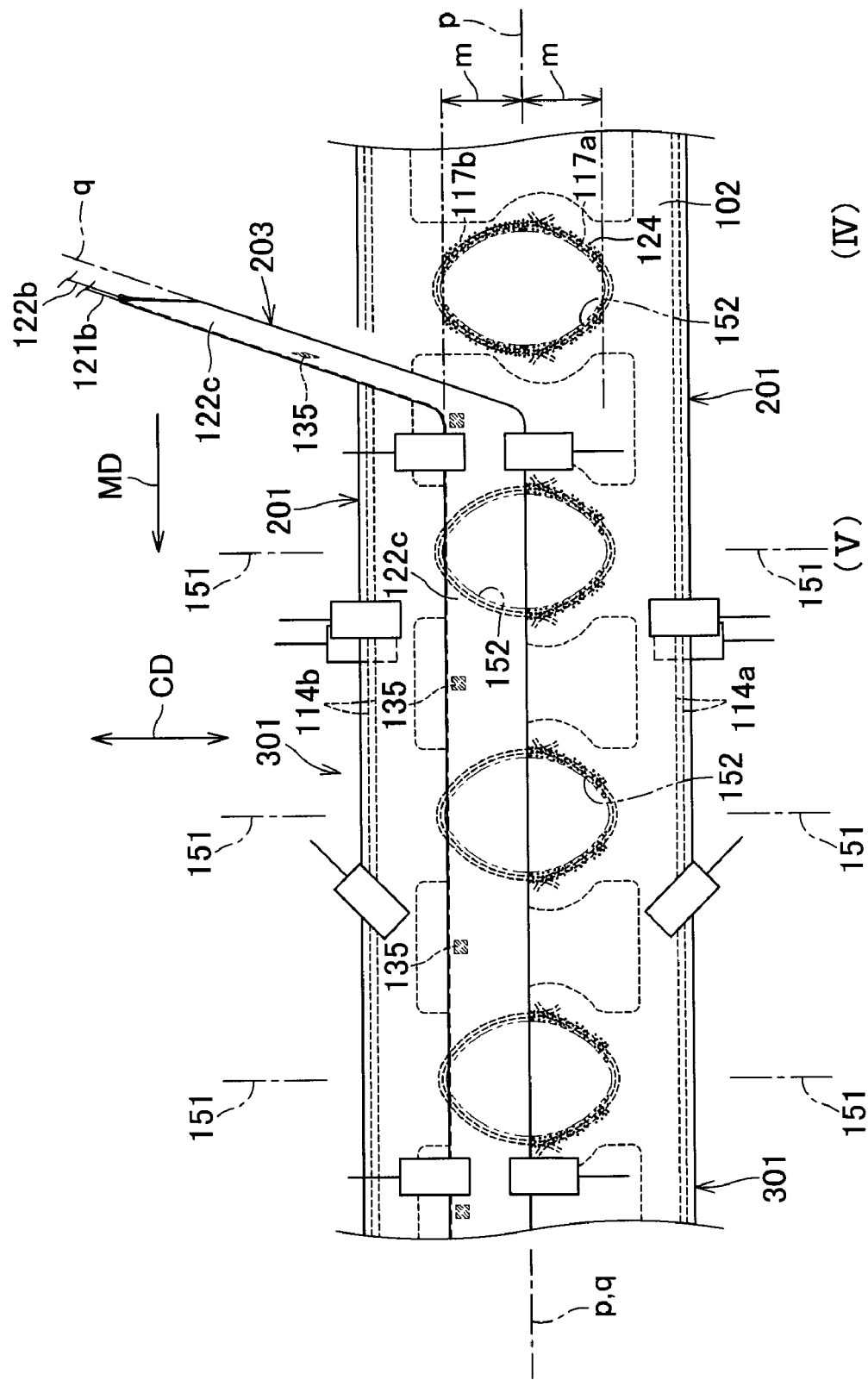
FIG. 8 is a diagram illustrating the step following up the step illustrated in FIG. 7.

In a fourth step IV illustrated by FIG. 8, the first web 201 corresponding to the continuous inner sheet 102 is coated immediately outside and along the loop-shaped imaginary line 152 with hot melt adhesive 124. The range over which the continuous inner sheet 102 is coated with the adhesive 124 extends on both sides from the first center line p-p in the cross direction CD by a distance m, preferably so that this range extends sufficiently to cover the elastic members 117a, 117b.

In a fifth step V illustrated by FIG. 8, the third web 203 is superposed upon the continuous inner sheet 102 in the first web 201 so that the second center line q-q falls in which the first center line p-p and the seal region 135 is located in the middle between the adjacent imaginary lines 151, 151, in other words, located in the middle of the chassis 10a as viewed in the transverse direction thereof. The first web 201 and the third web 203 are bonded together by the adhesive 124 coated on the first web 201 and thereby a first composite web 301 is obtained. In the first composite web 301, the first web 201 and the third web 203 are free from each other in the remaining region with respect to the region occupied by the adhesive 124. Alternatively, the third web 203 may be bonded to the first web 201 in the vicinity of the middle between each pair of the adjacent imaginary lines 151, 151. The elastic members 114a, 114b, 117a, 117b, 121b, 122b are indicated by chained lines as if seen through but the adhesive 124 is not indicated. It should be understood that the first center line p-p and the second center line q-q to fall in with each other in the fifth step V may be misaligned with each other so far as such alignment does not disturb making and use of the pants-type diaper.

Figure 9:
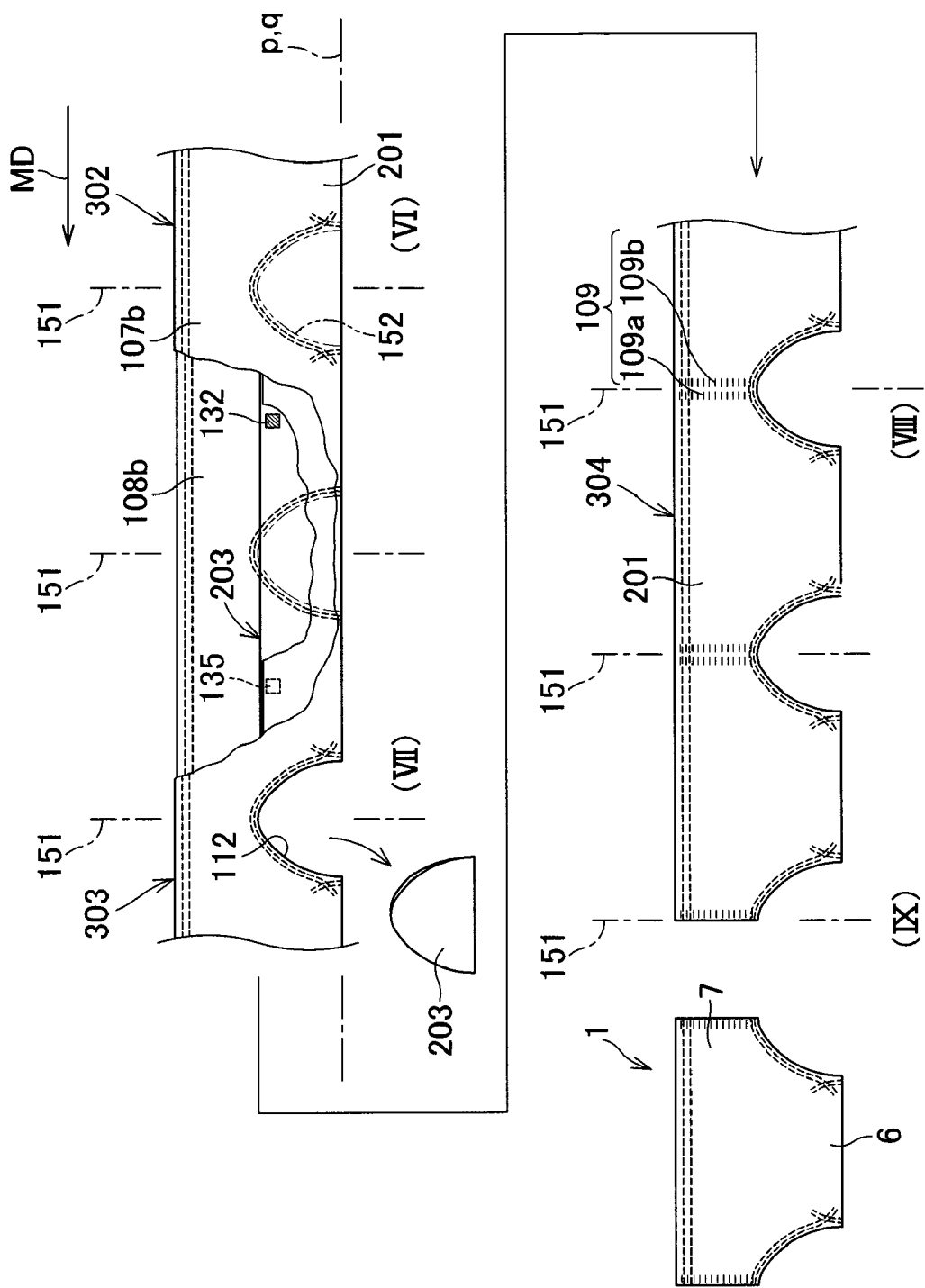
FIG. 9 is a diagram illustrating an alternative embodiment of the step illustrated in FIG. 8.

In a sixth step VI illustrated by FIG. 9, the first composite web 301 is folded back onto itself along a folding guide line defined by the first center line p-p of the first web 201 with the third web 203 inside wherein the first web 201 and the third web 203 superposed upon each other are bonded together by the adhesive 124 (See FIG. 8) to obtain a second composite web 302. In the course of bonding, the first web 201 and the third web 203 may be compressed in thickness direction thereof to assure desired bonding effect. The loop-shaped imaginary line 152 described on the first web 201 to be symmetric about the first center line p-p now describes on the second composite web 302 a circular arc which is convex from a chord defined by the first center line p-p toward the edges 107b, 108b (See FIG. 5) falling in with each other so as to describe a substantially semicircular shape which is bilaterally symmetric as viewed in the machine direction. The region in which the first web 201 and the third web 203 are bonded to each other by the adhesive 124 in the sixth step VI is superposed on the region in which the first web 201 and the third web 203 are bonded to each other by the adhesive 124 in the fifth step V. In the sixth step VI also, the first web 201 and the third web 203 are free from each other in the remaining region with respect to the region occupied by the adhesive 124.

In the seventh step VII illustrated by FIG. 9, the section surrounded by the substantially circular imaginary line 152 is clipped out from the second composite web 302 to obtain the third composite web 303 having a substantially semicircular notch 112. This clipping step generates scrap in the form of substantially semicircular web pieces 215 clipped out from the second composite web 302. Each notch 112 is substantially semicircular shaped and symmetric about the imaginary line 151.

In the eighth step VIII illustrated by FIG. 9, the inner surface of the first web 201 folded in two is bonded to itself on both sides of the imaginary line 151 along two seal regions each comprising a plurality of seal stripes 109a, 109b to obtain a fourth composite web 304. To achieve the desired bonding effect, appropriate bonding means such as sonic sealing technique or hot melt adhesive may be used. A plurality of seal stripes 109a and a plurality of seal stripes 109b form linear seal regions 109, respectively, which are belt-like regions extending in the cross direction CD.

In the step IX illustrated by FIG. 9, the fourth web 304 is cut along the imaginary line 151 bisecting the seal region 109 in the machine direction MD to obtain the individual pants-type diaper 1.

The chassis 10a and the sheet piece 20 in the pants-type diaper 1 shown in FIG. 1 is obtained from the first web 201 and the second web 202, respectively, used in the steps illustrated by FIGS. 5 through 9. The inner sheet 2, the outer sheet 3 and the liquid-absorbent core 4 are obtained from the continuous inner sheet 102, the continuous outer sheet 103 and the liquid-absorbent core 104, respectively. The periphery of the circular notch 112 is destined to form the peripheries 13 of the leg-holes 12 in the diaper 1 and the elastic members 117a, 117b are respectively divided in right and left halves along the imaginary line 151 to form the front elastic members 17a and the rear elastic members 17b of the respective leg elastic members 17 shown in FIG. 2. The elastic members 114a, 114b in the first web 201 correspond to the waist elastic members 14a, 14b in FIG. 1, respectively.

The method for making the pants-type diaper exemplarily illustrated allows the first web 201, the second web 202, the third web 203 and the like to be maintained under tension in the machine direction MD as well as in the cross direction CD by the feed rolls and the tentering rolls disposed at appropriate locations along the edges of these webs, respectively. There is no need for chucks or the like used only for the purpose of keeping these first and second webs 201, 202 under tension and therefore both the first web 201 and the second web 202 are not wasted in the course of making the pants-type diaper 1. In addition, the pants-type diaper 1 made by the method of the invention advantageously facilitates the external genitals and the anus of the wearer to be exactly opposed to the front opening 33 and the rear opening 34, respectively, of the pocket 20a in the diaper 1 (See FIGS. 1, 3 and 4). According to the exemplarily illustrated method, the second web 202 destined to form the pocket 20a is folded in two so as to obtain the third web 203 carrying the seal region 135 before the third web 203 is bonded to the first web 201. In this way, formation of the seal region 35 in the pants-type diaper 1 would not be accompanied with any significant difficulty.

The present invention is not limited to the steps exemplarily illustrated but contents of the respective steps as well as the order of these steps may be variously modified without departing from the object of the present invention. For example, in the step IV, the first web 201 may be previously coated with the adhesive 124 along the segment of the loop-shaped imaginary line 152 extending above the first center line p-p and then the third web 203 may be bonded to the first web 201. Thereafter, the first web 201 may be coated with the adhesive 124 along the segment of the loop-shaped imaginary line 152 extending below the first center line p-p and then the first web 201 may be folded back along the first center line p-p so that the first web 201 and the third web 203 thus superposed on each other may be bonded to each other. In the step modified in this manner, even when the first web 201 and the third web 203 are bonded to each other under a compression, the presence of the adhesive 124 coated on the first web 201 would not pose an impediment on the operation of compression. Furthermore, the step VII and the step VIII may be order-reversed in the method exemplarily illustrated so that the notch 112 may be formed after the second composite web 302 has been formed with the seal region 109. In the case of the second web 202 is formed by a nonwoven fabric made of thermoplastic synthetic fibers, the respective halves of the second web 202 may be bonded together by sonic sealing technique instead of the bonding agent 132.

The invention claimed is:

1. A method for making a disposable pants-type diaper comprising the continuous steps of:
preparing a chassis having a crotch region having a back-and-forth direction and a transverse direction which is orthogonal to said back-and-forth direction, a front waist region extending forward from said crotch region and a rear waist region extending rearward from said crotch region wherein transversely opposite side edges of said crotch region extend in said back-and-forth direction,
folding back said chassis about said crotch region in said back-and-forth direction,
bonding respective inner surfaces of said front and rear waist regions to each other along transversely opposite side edges of said front and rear waist regions to make said chassis in a pants-shape and
providing a sheet piece on said inner surface in said crotch region to form a pocket adapted to receive body waste,
said continuous steps for making said disposable pants-type diaper further comprising the steps of:
a) continuously feeding a first web in a machine direction wherein said first web having a dimension in a cross direction orthogonal to said machine direction bisected by a first center line is adapted to provide successively a plurality of said chassis each having said transverse direction in coincidence with said machine direction as said first web is cut at regular pitches in said machine direction,
b) continuously feeding a second web in said machine direction wherein said second web comprising a plurality of said sheet pieces contiguous one to another in said transverse direction,
c) folding said second web back onto itself along a first folding guide line defined by a second center line bisecting said second web in said cross direction and locally bonding respective halves of second web to each other at seal regions along respective edges thereof at the same pitches so as said pitches so as to obtain a folded third web having said locally seal regions,
d) superposing said first web and said folded third web upon each other so that said first center line falls in with said first folding guide line formed by said third web in said step c) and said seal regions of said third web fall in with middle regions of respective said chassis,
e) locally bonding said third web to said first web in regions thereof destined to form the transversely opposite side edges of said crotch region in said chassis or in regions located aside toward middle regions of respective said chassis as viewed in said machine direction so as to obtain a first composite web having said third web spaced from regions of said first web destined to define said chassis between said regions in which said first web and said third web are bonded to each other,
f) folding back said first composite web along a second folding guide line defined by said first center line with said third web inside and locally bonding said first web to said third web in regions falling in with said regions in which said first web and said third web are bonded to each other in said step e) so as to obtain a second composite web having said third web spaced from regions of said first web destined to define said chassis between said regions in which said first web and said third web are bonded to each other,
g) clipping out a substantially semicircular web piece having a straight line defined by said second folding guide line and an arc being convex toward side edges of the first web in said cross direction so as to form side edges of said crotch region opposed to each other in said machine direction and thereby to obtain a third composite web,
h) bonding opposite inner surfaces of said first web folded back onto itself in said third composite web to each other along respectively opposite side edges of said front and rear waist regions in each pair of adjacent said chassis so as to obtain a fourth composite web formed with a linear seal region extending said cross direction, and
i) cutting said fourth composite web along a cutting line extending in said cross direction at middle of said seal region as viewed in said machine direction to obtain individual said pants-type diapers successively.

2. A method for making a disposable pants-type diaper comprising the continuous steps of:
preparing a chassis having a crotch region having a back-and-forth direction and a transverse direction which is orthogonal to said back-and-forth direction, a front waist region extending forward from said crotch region and a rear waist region extending rearward from said crotch region wherein transversely opposite side edges of said crotch region extend in said back-and-forth direction,
folding back said chassis about said crotch region in said back-and-forth direction,
bonding respective inner surfaces of said front and rear waist regions to each other along transversely opposite side edges of said front and rear waist regions to make said chassis in a pants-shape and
providing a sheet piece on said inner surface in said crotch region to form a pocket adapted to receive body waste,
said continuous steps for making said disposable pants-type diaper further comprising the steps of:
a) continuously feeding a first web in a machine direction wherein said first web having a dimension in a cross direction orthogonal to said machine direction bisected by a first center line is adapted to provide successively a plurality of said chassis each having said transverse direction in coincidence with said machine direction as said first web is cut at regular pitches in said machine direction,
b) continuously feeding a second web in said machine direction wherein said second web comprising a plurality of said sheet pieces contiguous one to another in said transverse direction,
c) folding said second web back onto itself along a first folding guide line defined by a second center line bisecting said second web in said cross direction and locally bonding respective halves of second web to each other at seal regions along respective edges thereof at the same pitches as said pitches so as to obtain a third web having said locally seal regions,
d) superposing said first web and said third web upon each other so that said first center line falls in with said first folding guide line formed by said third web in said step c) and said seal regions of said third web fall in with middle regions of respective said chassis, e) locally bonding said third web to said first web in regions thereof destined to form the transversely opposite side edges of said crotch region in said chassis or in regions located aside toward middle regions of respective said chassis as viewed in said machine direction so as to obtain a first composite web having said third web spaced from regions of said first web destined to define said chassis between said regions in which said first web and said third web are bonded to each other, f) folding back said first composite web along a second folding guide line defined by said first center line with said third web inside and locally bonding said first web to said third web in regions falling in with said regions in which said first web and said third web are bonded to each other in said step e) so as to obtain a second composite web having said third web spaced from regions of said first web destined to define said chassis between said regions in which said first web and said third web are bonded to each other, g) bonding opposite inner surfaces of said first web folded back onto itself in said third composite web to each other along respectively opposite side edges of said front and rear waist regions in each pair of adjacent said chassis so as to obtain a fourth composite web formed with a linear seal region extending said cross direction, h) clipping out a substantially semicircular web piece having a straight line defined by said second folding guide line and an arc being convex toward side edges of the first web in said cross direction so as to form side edges of said crotch region opposed to each other in said machine direction and thereby to obtain a third composite web, and i) cutting said fourth composite web along a cutting line extending in said cross direction at middle of said seal region as viewed in said machine direction to obtain individual said pants-type diapers successively.

3. The method as recited by claim 1, wherein said step of feeding said second web further comprises feeding (i) an inelastic web of the second web in said machine direction and (ii) elastic members of the second web, said elastic members provided along opposite side edges of the inelastic web extending in parallel to each other in said machine direction and attached under tension to said opposite side edges of the inelastic web.

4. The method as recited by claim 1, wherein in said step of feeding said second web, said second web, which is elastically stretchable and contractible in said machine direction, is fed under tension in said machine direction.

5. The method as recited by claim 1, wherein said first web and said third web are locally bonded in said middle region of said crotch region in said chassis as viewed in said back-and-forth direction.

6. The method as recited by claim 1, wherein in said step c) of locally bonding the halves of said second web, said halves of the second web are bonded to each other in said seal regions in said third composite web by providing a plurality of bonding agents.

7. The method as recited in claim 6, wherein said bonding agents are provided on the second web and closer to one of said edges in the cross direction of the second web than the first folding guide line.

8. The method as recited in claim 1, wherein said third web is boned to said first web by adhesive that is provided on the regions of the first web in said step e) and extends all the way between opposite side edges of the second web in the cross direction.

9. The method as recited in claim 3, wherein
said second web is boned to said first web by adhesive that is provided on the regions of the first web in said step d) and extends all the way between opposite side edges of the second web in the cross direction, and
said adhesive overlaps with an intermediate section of each of the elastic members, without overlapping both opposite end sections of each said elastic member in the cross direction.

10. The method as recited in claim 3, wherein
each of said elastic members is formed in a loop shape which has first and second opposite end sections in the cross direction and an intermediate section,
said first end section extends beyond one side edge of the third web in the cross direction, and said second end section and a half of the intermediate section extend beyond the first folding guide line in the cross direction, and
the other half of the intermediate section of the elastic members overlaps with the third web.

11. The method as recited in claim 1, wherein a width of the second web in the cross direction is less that that of each chassis adapted to be formed by the first web.

12. The method as recited in claim 1, wherein the halves of the second web are bonded to each other at the seal regions on the second web between adjacent said regions where said first and third web are bonded together in said step d).

13. The method as recited in claim 1, wherein the halves of said second web are directly bonded to each other in the folded third web in said step c).

14. The method as recited in claim 2, wherein the halves of said second web are directly bonded to each other in the folded third web in said step c).

* * * * *